(12) United States Patent (10) Patent No.: US 9,134,203 B2
Smith et al. (45) Date of Patent: Sep. 15, 2015

(54) BLOOD SAMPLE TUBE INDICATOR

(71) Applicant: ABBOTT LABORATORIES, Abbott Park, IL (US)

(72) Inventors: Bradley Smith, Rhome, TX (US); Sarah Benson, Grapevine, TX (US)

(73) Assignee: Abbott Laboratories, Abbott Park, IL (US)

( * ) Notice: Subject to any disclaimer, the term of this patent is extended or adjusted under 35 U.S.C. 154(b) by 220 days.

(21) Appl. No.: 13/727,416

(22) Filed: Dec. 26, 2012

(65) Prior Publication Data

US 2013/0167768 A1 Jul. 4, 2013

Related U.S. Application Data

(60) Provisional application No. 61/580,778, filed on Dec. 28, 2011.

(51) Int. Cl.
*G01N 1/10* (2006.01)
*B01L 3/14* (2006.01)
(Continued)

(52) U.S. Cl.
CPC ............ *G01N 1/10* (2013.01); *A61B 5/1411* (2013.01); *A61B 5/1438* (2013.01); *A61B 5/15003* (2013.01); *A61B 5/154* (2013.01); *A61B 5/150351* (2013.01); *A61B 5/150755* (2013.01); *A61B 5/150778* (2013.01); *A61B 5/150786* (2013.01)

(58) Field of Classification Search
CPC .. G01N 1/10; A61B 5/1438; A61B 5/150778; A61B 5/150786; A61B 5/150351; B01L 3/5453; B01L 3/5457; B01L 2300/041; B01L 2300/042; B01L 2300/046; B65D 41/32

USPC ........... D24/224; 116/201, DIG. 41; 422/549, 422/550, 568, 913–917, 941, 945
See application file for complete search history.

(56) References Cited

U.S. PATENT DOCUMENTS 3,415,627 A * 12/1968 Rait ................................. 422/72
3,799,426 A * 3/1974 Pates et al. ..................... 229/4.5
5,019,243 A 5/1991 McEwen et al.
(Continued)

OTHER PUBLICATIONS

Preanalytics Catalogue by (Grenier bio-one) Dec. 1, 2011 Accessed Apr. 16, 2013, entire document, especially p. 8—para25 http:l/web. archive.orglweb/20111201 060 145/http:/lgbo.com/documents/ 980042_VACU ETTEKatalog_rev05_08_2010_e_small.pdf.
(Continued)

*Primary Examiner* — Daniel S Larkin
(74) *Attorney, Agent, or Firm* — Klintworth & Rozenblat IP LLC

(57) ABSTRACT

A blood sample apparatus includes a blood sample tube, a cap, and an indicator. The blood sample tube has an exterior surface, an inner cavity disposed within the exterior surface, and an open end. The cap closes the open end of the blood sample tube. The inner cavity is under a vacuum-seal or connected to a suction device for drawing a blood sample into the inner cavity. The indicator is attached to or includes a portion of the blood sample tube for indicating a type, or lack thereof, of blood additive disposed within the inner cavity. When the cap is removed from the open end of the blood sample tube the indicator remains attached to or still includes the portion of the blood sample tube. If the indicator is a label it extends around at least half of a perimeter of the blood sample tube.

19 Claims, 11 Drawing Sheets

(51) Int. Cl.
*A61B 5/15* (2006.01)
*A61B 5/154* (2006.01)

(56) References Cited

U.S. PATENT DOCUMENTS 5,038,794 A * 8/1991 Van Valkenburg ............ 600/576
7,445,152 B2 * 11/2008 Golabek et al. .......... 235/462.01

2006/0091669 A1 * 5/2006 Wilkinson ..................... 283/74
2008/0003148 A1 1/2008 Dause
2008/0142469 A1 * 6/2008 Zeligson ....................... 215/217
2010/0323437 A1 12/2010 Nakae et al.

OTHER PUBLICATIONS

Search Report dated May 2, 2013, PCT/US2012/71850.

* cited by examiner

BLOOD SAMPLE TUBE INDICATOR

CROSS REFERENCES TO RELATED APPLICATIONS

The Present Application is based on and claims the benefit of priority from U.S. Provisional Patent Application Ser. No. 61/580,778, entitled "BLOOD SAMPLE TUBE INDICATOR" and filed on Dec. 28, 2011 with the United States Patent and Trademark Office, the contents of which are hereby incorporated by reference in their entirety to the extent permitted by law.

FIELD OF THE DISCLOSURE

This disclosure relates to an indicator for indicating a type, or lack thereof, of a blood additive disposed within a blood sample tube.

BACKGROUND OF THE DISCLOSURE

Blood sample tubes carry a variety of blood additives for mixing with the blood samples inserted into the blood sample tubes. It is important to keep track of which additive is contained within which blood sample tube for testing and recording purposes. Some existing blood sample tubes use a variety of cap colors to indicate which additive is contained within which blood sample tube. However, once the cap of the blood sample tube is removed the cap is no longer there to indicate which additive is contained within the blood sample tube. Other blood sample tubes use a color indication on the manufacturer's label disposed on the blood sample tube to indicate the additive disposed within the blood sample tube. However, these labels only cover a small portion of the blood sample tube and often get covered up by the testing laboratory's sample barcode label making it difficult to know which additive is contained within the blood sample tube.

There is a need for an apparatus and method which will resolve one or more issues of the existing art.

SUMMARY OF THE DISCLOSURE

In one embodiment, a blood sample apparatus comprises a blood sample tube, a cap, and an indicator. The blood sample tube has an exterior surface, an inner cavity disposed within the exterior surface, and an open end. The cap closes the open end of the blood sample tube. The inner cavity is under a vacuum-seal or connected to a suction device for drawing a blood sample into the inner cavity. The indicator is attached to or comprises a portion of the blood sample tube for indicating a type, or lack thereof, of blood additive disposed within the inner cavity. When the cap is removed from the open end of the blood sample tube the indicator remains attached to or still comprises the portion of the blood sample tube. If the indicator comprises a label it extends around at least half of a perimeter of the blood sample tube.

In another embodiment, an automatic blood sample handling system comprises a blood sample tube, an input module, a de-cap device, and an identification device. The blood sample tube comprises an exterior surface, an inner cavity disposed within the exterior surface holding a blood additive or a blood sample, a cap closing an open end of the blood sample tube, and an indicator attached to or comprising a portion of the blood sample tube. If the indicator comprises a label it extends around at least half of a perimeter of the blood sample tube. The input module is for supplying the blood sample tube. The de-cap device is for removing the cap from the blood sample tube leaving the indicator attached to or still comprising the portion of the blood sample tube. The identification device is for identifying a type, or lack thereof, of the blood additive disposed within the inner cavity based on the indicator attached to or comprising the portion of the blood sample tube.

In an additional embodiment, a method of automatically identifying a type, or lack thereof, of blood additive disposed within a blood sample tube is provided. In one step, a cap is automatically removed from an open end of a blood sample tube leaving an indicator attached to or comprising a portion of the blood sample tube. If the indicator comprises a label it extends around at least half of a perimeter of the blood sample tube. In another step, a type, or lack thereof, of blood additive disposed within the blood sample tube is automatically identified based on the indicator.

In still another embodiment, an automatic blood sample handling system comprises a blood sample tube, an input module, and a marking device. The blood sample tube comprises an exterior surface, an inner cavity disposed within the exterior surface holding a blood additive or a blood sample, and a cap closing an open end of the blood sample tube. The input module is for supplying the blood sample tube. The marking device is for automatically marking the blood sample tube with an indicator indicating a type, or lack thereof, of the blood additive disposed within the blood sample tube.

In yet another embodiment, a method is provided of automatically identifying a type, or lack thereof, of blood additive disposed within a blood sample tube. In one step, a characteristic of a cap attached to and closing an open end of a blood sample tube is automatically identified. In another step, the blood sample tube is automatically marked with an indicator, based on the identified characteristic of the cap, indicating a type, or lack thereof, of a blood additive disposed within the blood sample tube.

These and other features, aspects and advantages of the disclosure will become better understood with reference to the following drawings, description and claims.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

Figure 1:
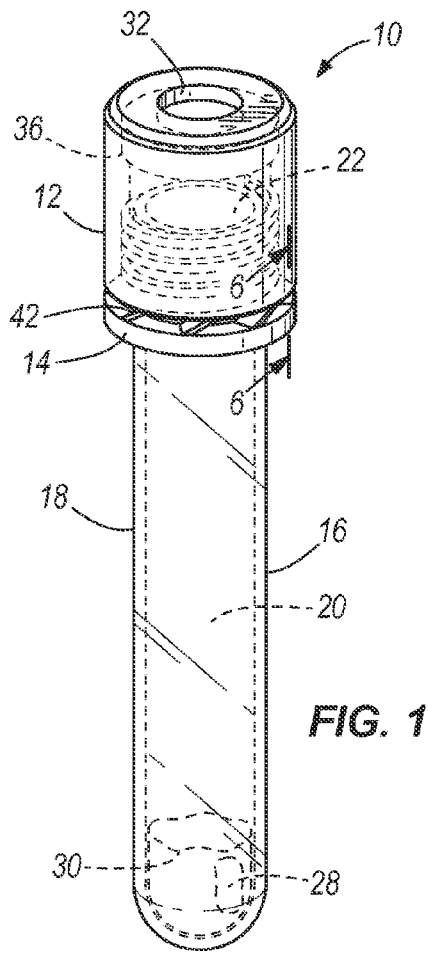
FIG. 1 illustrates a front perspective view of one embodiment of a blood sample apparatus with a cap and an indicator, attached to the cap, both attached to a blood sample tube.
Figure 2:
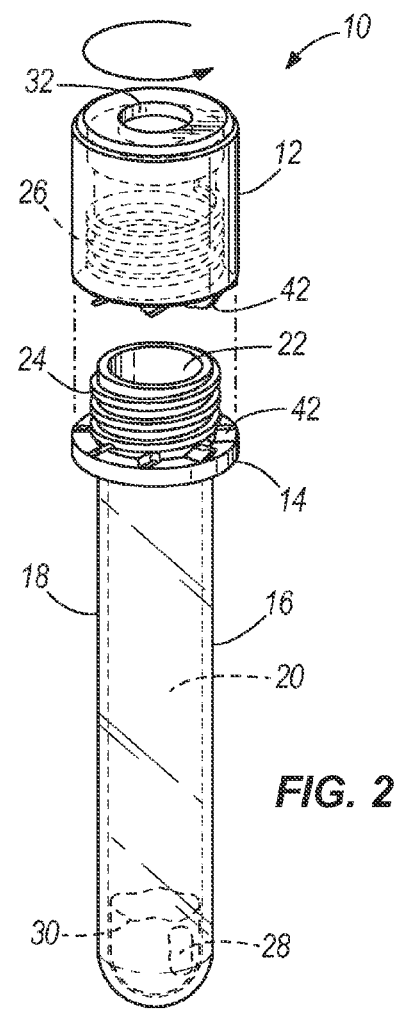
FIG. 2 illustrates the front perspective view of FIG. 1 with the cap detached from the blood sample tube and the indicator detached from the cap, but still attached to the blood sample tube.

FIG. 1 illustrates a front perspective view of one embodiment of a blood sample apparatus 10 with a cap 12 and an indicator 14, attached to the cap 12, both attached to a blood sample tube 16. FIG. 2 illustrates the front perspective view of FIG. 1 with the cap 12 detached from the blood sample tube 16 and the indicator 14 detached from the cap 12 but still attached to the blood sample tube 16. The cap 12 is made of polyethylene and has an outer diameter of 15 mm. In other embodiments, the cap 12 may be made of varying materials, such as polypropylene, and may have an outer diameter ranging between 9 and 25 mm. In still other embodiments, the cap 12 may be made of differing materials and may be of varying shapes or sizes. The indicator 14 is in the form of a ring, is made of polyethylene and has an outer diameter of 15 mm. In other embodiments, the indicator 14 may be made of varying materials, such as polypropylene, and may have an outer diameter ranging between 9 and 25 mm. In still other embodiments, the indicator 14 may be made of differing materials and may be of varying shapes or sizes. The blood sample tube 16 is made of polyethylene terephthalate (PET) and has a height of 75 mm and an outer diameter of 13 mm. In other embodiments, the blood sample tube 16 may be made of varying materials, such as polypropylene, and may have a height ranging between 60 to 100 mm and an outer diameter ranging between 10 to 17 mm. In still other embodiments, the blood sample tube 16 may be made of differing materials and may be of varying shapes or sizes.

As shown in FIGS. 1 and 2 collectively, the blood sample tube 16 comprises an exterior surface 18, an inner cavity 20 disposed within the exterior surface 18, and an open end 22. As shown in FIG. 1, when the cap 12 is attached to the sample tube 16 the cap 12 covers the open end 22 of the blood sample tube 16 while the indicator 14 is attached to the cap 12. As shown in FIG. 2, when the cap 12 is detached and removed from the sample tube 16 the open end 22 of the blood sample tube 16 is exposed and the indicator 14 detaches from the cap 12 and remains attached to the blood sample tube 16. Both the blood sample tube 16 and the cap 12 have threads 24 and 26 for attaching the cap 12 to the blood sample tube 16. In other embodiments, the cap 12 may be attached to the blood sample tube 16 using a friction fit, a snapping mechanism, or through other connection mechanisms. A blood additive 28 and a blood sample 30, taken from a patient, may be disposed in the inner cavity 20 of the blood sample tube 16. The blood additive 28 may comprise any type of blood additive added to a blood sample 30 for testing purposes. Exemplary blood additives 28 include potassium EDTA, lithium heparin, and sodium citrate.

Figure 3:
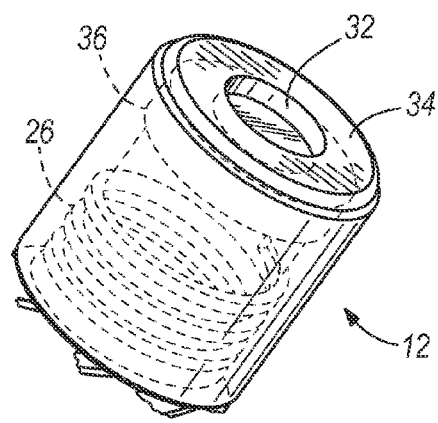
FIG. 3 illustrates a top perspective view of the cap of FIG. 1.
Figure 4:
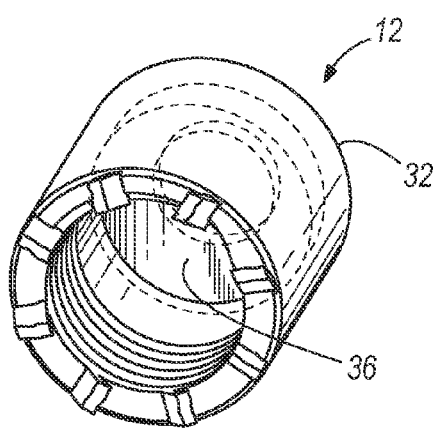
FIG. 4 illustrates a bottom perspective view of the cap of FIG. 1.

FIG. 3 illustrates a top perspective view of the cap 12 of FIG. 1. FIG. 4 illustrates a bottom perspective view of the cap 12 of FIG. 1. As shown collectively in FIGS. 3 and 4, a hole 32 extends through a top surface 34 of the cap 12. The hole 32 may have a diameter ranging between 5 to 12 mm. In still other embodiments, the hole 32 may comprise varying shapes or sizes. A rubber gasket 36 is disposed within the cap 12 covering the hole 32 of the cap 12. The rubber gasket 36 is shaped like a cylindrical plug, and has a size to mate firmly with the inner diameter of the blood sample tube 16 (shown in FIGS. 1 and 2). In other embodiments, the rubber gasket 36 may be made of varying materials, such as urethane, may be shaped like a gasket inside the cap 12, and may have an outer diameter ranging between 8 and 22 mm. In still other embodiments, the rubber gasket 36 may be made of differing materials and may be of varying shapes or sizes. The rubber gasket 36 allows the cap 12 to be attached to the blood sample tube 16, as shown in FIG. 1, with an air-tight connection. The inner cavity 20 of the blood sample tube 16 of FIG. 1 is under a vacuum-seal so that when a blood removal tube, catheter, or needle (not shown) is extended through the hole 32 through the rubber gasket 36 into the inner cavity 20 of the blood sample tube 16, a blood sample 30 being removed from a patient (not shown) will be sucked into the inner cavity 20.

Figure 5:
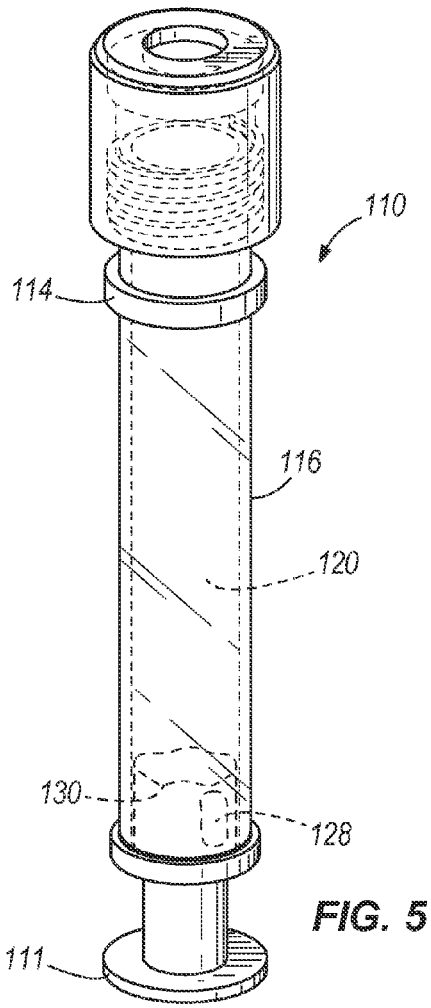
FIG. 5 illustrates a top perspective view of another embodiment of a blood sample apparatus.

FIG. 5 illustrates a top perspective view of another embodiment of a blood sample apparatus 110 which, rather than using a vacuum-seal, uses a blood suction device 111 for drawing a blood sample 130 into the inner cavity 120 of the blood sample tube 116. The blood suction device 111 may comprise a syringe plunger or other type of blood suction device for suctioning a blood sample 130 into the inner cavity 120 of the blood sample tube 116. The blood sample apparatus 110 may utilize an indicator 114 for indicating the presence of an additive 128 disposed within the inner cavity 120 of the blood sample tube 116. The indicator 114 may be attached to the blood sample tube 116 using any of the embodiments disclosed herein, or in other embodiments, through varying mechanisms.

Figure 6:
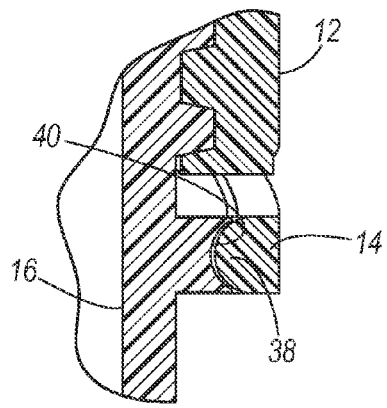
FIG. 6 illustrates a cross-sectional view along line 6-6 of the embodiment of FIG. 1.

FIG. 6 illustrates a cross-sectional view along line 6-6 of the embodiment of FIG. 1. The indicator 14 comprises a ring. In other embodiments, the indicator 14 may be of varying shapes or sizes. As shown in FIG. 6, when the cap 12 is attached to the blood sample tube 16, a mating portion 38 of the indicator 14 mates with a mating portion 40 of the blood sample tube 16. The mating portion 38 of the indicator 14 is sized to fit over the threads of the blood sample tube 16 to mate with the mating portion 40 of the blood sample tube 16 at which point a flap (which only allows one-way movement) of the mating portion 38 of the indicator 14 prevents the indicator 14 from coming dislodged from the mating portion 40 of the blood sample tube 16. The mating portion 38 of the indicator 14 comprises a male portion, and the mating portion 40 of the blood sample tube 16 comprises an internal female portion. Due to a tight friction fit of the mating portion 38 of the indicator 14 to the mating portion 40 of the blood sample tube 16, the flap of the mating portion 38 of the indicator 14 abutting against the mating portion 40 of the blood sample tube 16 only allowing one-way movement, and the indicator 14 being directly detachable attached to the cap 12 with a perforation 42 shown in FIGS. 1 and 2, when the cap 12 is rotatably detached from the blood sample tube 16 as shown in FIG. 2, the indicator 14 detaches from the cap 12 and remains attached to the blood sample tube 16. After the indicator 14 has been detached from the cap 12, the detachment of the indicator 14 from the cap 12 indicates that the cap 12 has been removed from the blood sample tube 16, even if the cap 12 is later reapplied to the blood sample tube 16, thereby providing tamper-resistance. In other embodiments, the indicator 14 may be directly detachably attached to the cap 12 using varying mechanisms.

As shown in FIG. 2, when the cap 12 is removed from the blood sample tube 16 the indicator 14 indicates a type, or lack thereof, of the blood additive 28 disposed within the inner cavity 20. For instance, the particular color of the indicator 14 indicates which type, or lack thereof, of the blood additive 28 is disposed within the inner cavity 20. As an example, if there were thirty different types of blood additives 28 which may be disposed within the inner cavity 20, thirty different colors would be used for thirty separate indicators 14 to indicate which of the thirty different types of blood additives 28 were disposed within the inner cavity 20, and a thirty-first color would be used for the thirty-first indicator 14 to indicate the lack of a blood additive 28 in the inner cavity 20. In other embodiments, any number of colors may be used for separate indicators 14 to indicate a type, or lack thereof, of blood additive 28 disposed within the inner cavity 20. In one embodiment, the color of the indicator 14 matches the color of the cap 12, with the color of the cap 12 also indicating a type, or lack thereof, of the blood additive 28 disposed within the inner cavity 20. As shown in FIG. 2, when the cap 12 is removed from the blood sample tube 16, the indicator 14 remains attached to the blood sample tube 16 so that the type of blood additive 28, or lack thereof, disposed within the inner cavity 20 of the blood sample tube 16 is still identifiable. In other embodiments, any characteristic of the indicator 14 may indicate the type of blood additive 28, or lack thereof, disposed within the inner cavity 20 of the blood sample tube 16. For instance, a varying size, a varying shape, or another varying identifying feature of the indicator 14 may be used to indicate the type of blood additive 28, or lack thereof, disposed within the inner cavity 20 of the blood sample tube 16.

Figures 7, 8, 9:
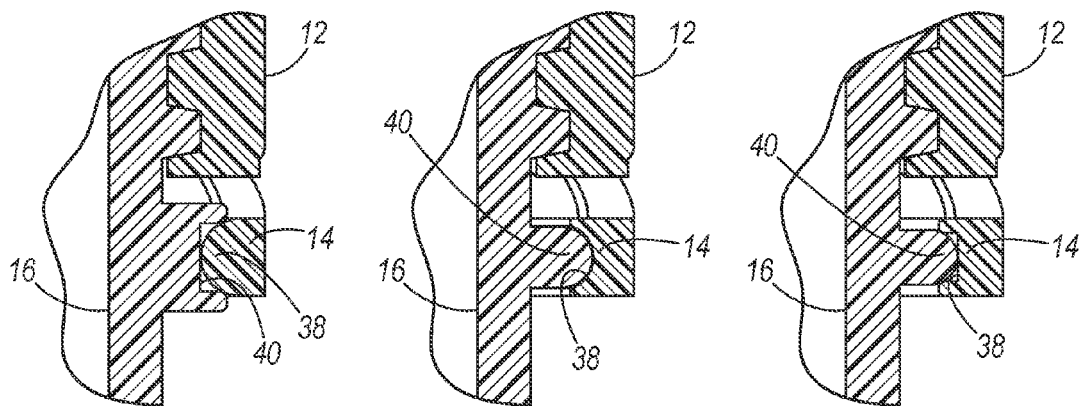
FIG. 7 illustrates an alternative embodiment which may be used for the cross-sectional view along line 6-6 of the embodiment of FIG. 1 to attach the indicator to the blood sample tube.
FIG. 8 illustrates another alternative embodiment which may be used for the cross-sectional view along line 6-6 of the embodiment of FIG. 1 to attach the indicator to the blood sample tube.
FIG. 9 illustrates another alternative embodiment which may be used for the cross-sectional view along line 6-6 of the embodiment of FIG. 1 to attach the indicator to the blood sample tube.

FIG. 7 illustrates an alternative embodiment which may be used for the cross-sectional view along line 6-6 of the embodiment of FIG. 1 to attach the indicator 14 to the blood sample tube 16. As shown in FIG. 7, when the cap 12 is attached to the blood sample tube 16, a mating portion 38 of the indicator 14 mates with a mating portion 40 of the blood sample tube 16. The mating portion 38 of the indicator 14 is sized to fit over the threads of the blood sample tube 16 to mate with the mating portion 40 of the blood sample tube 16 at which point a flap (which only allows one-way movement) of the mating portion 38 of the indicator 14 prevents the indicator 14 from coming dislodged from the mating portion 40 of the blood sample tube 16. The mating portion 38 of the indicator 14 comprises a male portion, and the mating portion 40 of the blood sample tube 16 comprises an external female portion. Due to a tight friction fit of the mating portion 38 of the indicator 14 to the mating portion 40 of the blood sample tube 16, the flap of the mating portion 38 of the indicator 14 abutting against the mating portion 40 of the blood sample tube 16 only allowing one-way movement, and the indicator 14 being directly detachable attached to the cap 12 with a perforation, when the cap 12 is detached from the blood sample tube 16, the indicator 14 detaches from the cap 12 and remains attached to the blood sample tube 16.

FIG. 8 illustrates another alternative embodiment which may be used for the cross-sectional view along line 6-6 of the embodiment of FIG. 1 to attach the indicator 14 to the blood sample tube 16. As shown in FIG. 8, when the cap 12 is attached to the blood sample tube 16, a mating portion 38 of the indicator 14 mates with a mating portion 40 of the blood sample tube 16. The mating portion 38 of the indicator 14 is sized to fit over the threads of the blood sample tube 16 to mate with the mating portion 40 of the blood sample tube 16 at which point a flap (which only allows one-way movement) of the mating portion 38 of the indicator 14 prevents the indicator 14 from coming dislodged from the mating portion 40 of the blood sample tube 16. The mating portion 38 of the indicator 14 comprises an internal female portion, and the mating portion 40 of the blood sample tube 16 comprises a male portion. Due to a tight friction fit of the mating portion 38 of the indicator 14 to the mating portion 40 of the blood sample tube 16, the flap of the mating portion 38 of the indicator 14 abutting against the mating portion 40 of the blood sample tube 16 only allowing one-way movement, and the indicator 14 being directly detachable attached to the cap 12 with a perforation, when the cap 12 is detached from the blood sample tube 16, the indicator 14 detaches from the cap 12 and remains attached to the blood sample tube 16.

FIG. 9 illustrates another alternative embodiment which may be used for the cross-sectional view along line 6-6 of the embodiment of FIG. 1 to attach the indicator 14 to the blood sample tube 16. As shown in FIG. 9, when the cap 12 is attached to the blood sample tube 16, a mating portion 38 of the indicator 14 mates with a mating portion 40 of the blood sample tube 16. The mating portion 38 of the indicator 14 is sized to fit over the threads of the blood sample tube 16 to mate with the mating portion 40 of the blood sample tube 16 at which point a flap (which only allows one-way movement) of the mating portion 38 of the indicator 14 prevents the indicator 14 from coming dislodged from the mating portion 40 of the blood sample tube 16. The mating portion 38 of the indicator 14 comprises an external female portion, and the mating portion 40 of the blood sample tube 16 comprises a male portion. Due to a tight friction fit of the mating portion 38 of the indicator 14 to the mating portion 40 of the blood sample tube 16, the flap of the mating portion 38 of the indicator 14 abutting against the mating portion 40 of the blood sample tube 16 only allowing one-way movement, and the indicator 14 being directly detachable attached to the cap 12 with a perforation, when the cap 12 is detached from the blood sample tube 16, the indicator 14 detaches from the cap 12 and remains attached to the blood sample tube 16. In other embodiments, the indicator 14 may be attached to the blood sample tube 16 with varying attachment mechanisms such as threads, snap-fits, friction fits, or other types of attachment mechanisms.

Figures 10, 11, 12:
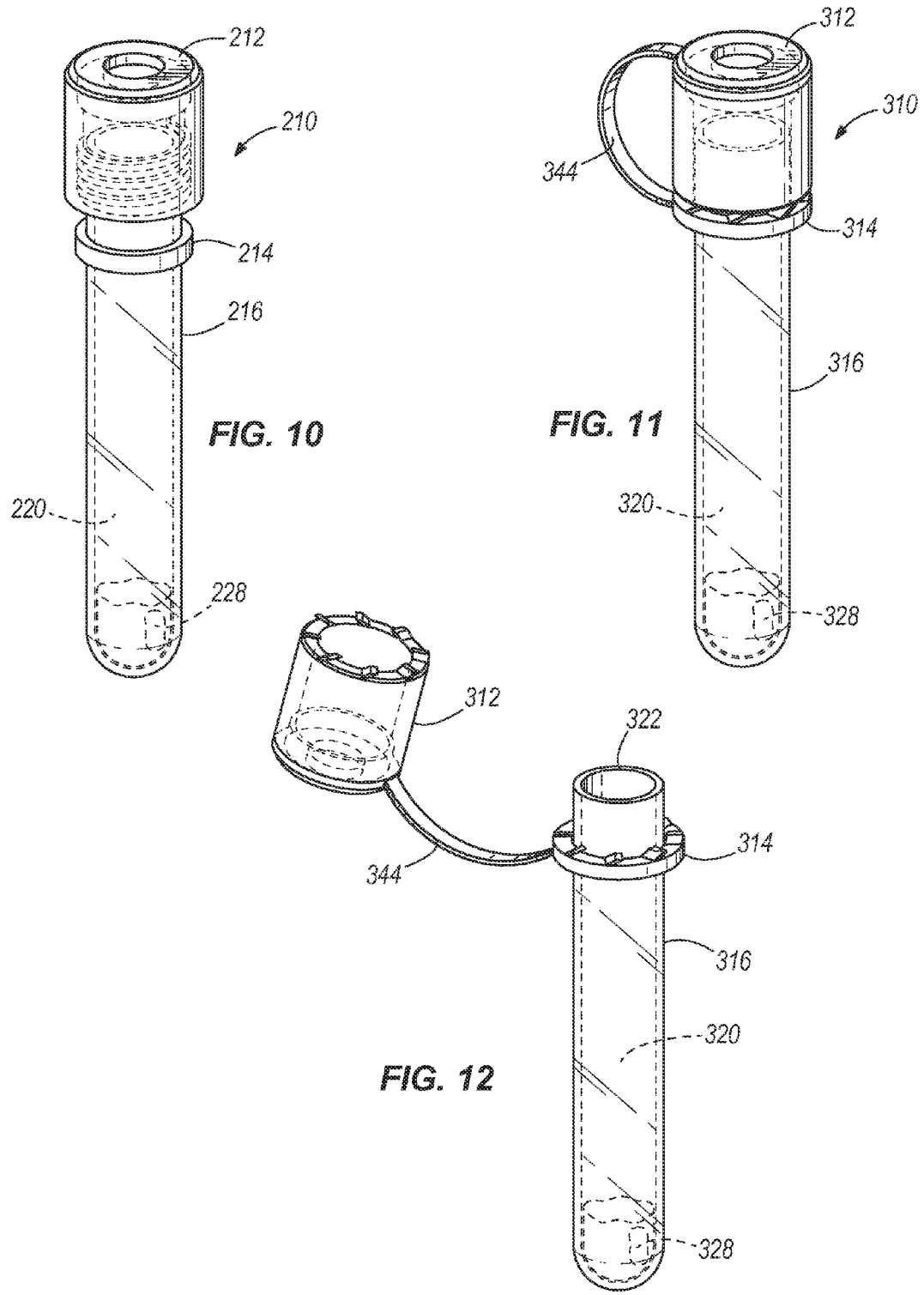
FIG. 10 illustrates a front perspective view of one embodiment of a blood sample apparatus having a cap and an indicator which are both directly attached to a blood sample tube without ever being directly attached to one another.
FIG. 11 illustrates a front perspective view of one embodiment of a blood sample apparatus having a cap attached to an indicator via a flexible member, with both the cap and the indicator being directly attached to a blood sample tube.
FIG. 12 illustrates the front perspective view of the embodiment of FIG. 11 with the cap having been removed from an open end of the blood sample tube.

FIG. 10 illustrates a front perspective view of one embodiment of a blood sample apparatus 210 having a cap 212 and an indicator 214 which are both directly attached to a blood sample tube 216 without ever being directly attached to one another. The indicator 214 may comprise a ring and may be directly attached to the blood sample tube 216 using the mechanisms discussed herein or other types of attachment mechanisms. The indicator 214 may be attached to the blood sample tube 216 using any of the embodiments disclosed herein, or in other embodiments, through varying mechanisms. In other embodiments, the indicator 214 may be in varying shapes and sizes. The indicator 214 does not provide tamper resistance since the indicator 214 is never attached to the cap 212. However, the indicator 214 still indicates a type, or lack thereof, of blood additive 228 disposed within an inner cavity 220 of the blood sample tube 216.

FIG. 11 illustrates a front perspective view of one embodiment of a blood sample apparatus 310 having a cap 312 attached to an indicator 314 via a flexible member 344, with both the cap 312 and the indicator 314 being directly attached to a blood sample tube 316. FIG. 12 illustrates the front perspective view of the embodiment of FIG. 11 with the cap 312 having been slideably removed from an open end 322 of the blood sample tube 316 with the cap 312 still being attached to the indicator 314 with the flexible member 344. The indicator 314, flexible member 344, and cap 312 may be made of polyethylene. The indicator 314 may be attached to the blood sample tube 316 using any of the embodiments disclosed herein, or in other embodiments, through varying mechanisms. In still other embodiments, the indicator 314, flexible member 344, and cap 312 may be made of varying materials, and may be of varying shapes or sizes. The indicator 314 indicates a type, or lack thereof, of blood additive 328 disposed within an inner cavity 320 of the blood sample tube 316.

Figures 13, 14:
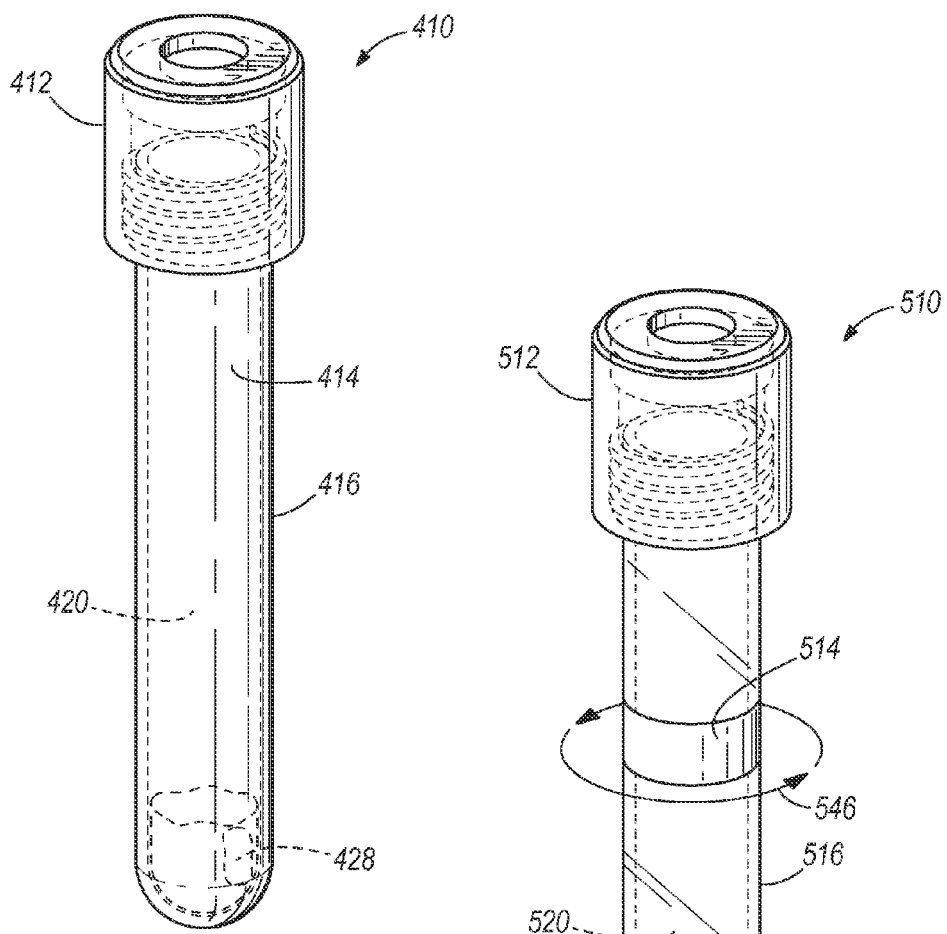
FIG. 13 illustrates a front perspective view of one embodiment of a blood sample apparatus having a cap attached to a blood sample tube.
FIG. 14 illustrates a front perspective view of one embodiment of a blood sample apparatus having a cap and an indicator both directly attached to a blood sample tube but not directly attached to one another.

FIG. 13 illustrates a front perspective view of one embodiment of a blood sample apparatus 410 having a cap 412 attached to a blood sample tube 416. The indicator 414 comprises a portion of the blood sample tube 416 for indicating a type, or lack thereof, of blood additive 428 disposed within the inner cavity 420 of the blood sample tube 416. The indicator 414 may comprise a color, shape, size, or other identifying feature of the portion of the blood sample tube 416. For instance, in one embodiment the entire blood sample tube 416, or a portion of the blood sample tube 416, may be colored to indicate a type, or lack thereof, of blood additive 428 disposed within the inner cavity 420 of the blood sample tube 416. In other embodiments, the blood sample tube 416 itself may be altered in various ways to indicate a type, or lack thereof, of blood additive 428 disposed within the inner cavity 420 of the blood sample tube 416. Since the indicator 414 comprises a portion of the blood sample tube 416, when the cap 412 is removed from the blood sample tube 416, the indicator 414 remains a portion of the blood sample tube 416 and is not removed from the blood sample tube 416.

FIG. 14 illustrates a front perspective view of one embodiment of a blood sample apparatus 510 having a cap 512 and an indicator 514 both directly attached to a blood sample tube 516 but not directly attached to one another. The indicator 514 comprises a label, made of paper, extending around at least half of the perimeter 546 of the blood sample tube 516. This overcomes the issues with existing labels which only cover a small portion of the blood sample tube, which do not extend around at least half of the perimeter of the blood sample tubes, and which are often covered up by the testing laboratory's sample barcode label making it difficult to know which additive is contained within the blood sample tube. In another embodiment, the indicator 514 may comprise a label extending around at least seventy-five percent of the perimeter 546 of the blood sample tube 516. In still another embodiment, the indicator 514 may comprise a label extending around the entire perimeter 546 of the blood sample tube 516 in the shape of a ring. The indicator 514 indicates a type, or lack thereof, of blood additive 528 disposed within an inner cavity 520 of the blood sample tube 516. In other embodiments, the indicator 514 may comprise labels made of varying materials, in varying size, or in varying shapes. In still other embodiments, as shown by some of the embodiments disclosed herein, one or more indicators may be utilized which do not consist of a label. In additional embodiments, as shown by some of the embodiments disclosed herein, one or more indicators may be utilized which do not comprise a label.

Figure 15:
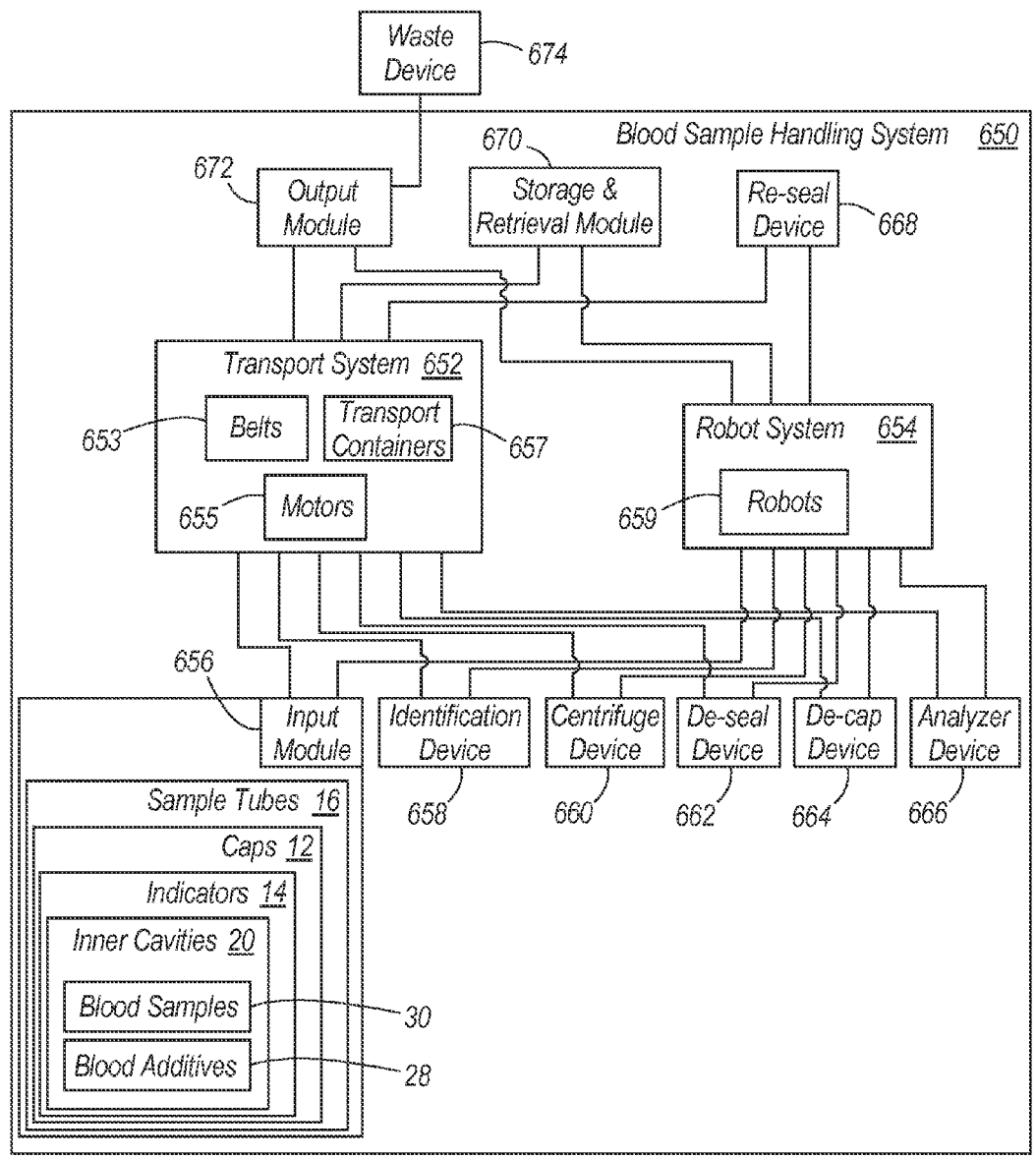
FIG. 15 illustrates a box diagram of one embodiment of an automatic blood sample handling system.

FIG. 15 illustrates a box diagram of one embodiment of an automatic blood sample handling system 650. The blood sample handling system 650 may comprise any type of automated blood sample processing system for processing and handling blood samples 30 contained in blood sample tubes 16 of blood sample apparatus 10. The blood sample tubes 16 and blood sample apparatus 10 processed and handled by the blood sample handling system 650 may comprise any of the variations disclosed herein. The blood sample handling system 650 comprises a transport system 652, a robot system 654, an input module 656, an identification device 658, a centrifuge device 660, a de-seal device 662, a de-cap device 664, at least one analyzer device 666, a re-seal device 668, a storage and retrieval module 670, and an output module 672. It is noted that any of the components of the blood handling system 650 may comprise their own processor/controller. In other embodiments, separate processor/controllers may be used to control the blood handling system 650.

The transport system 652 comprises a transport system for transporting blood sample tubes 16 between the input module 656, the identification device 658, the centrifuge device 660, the de-seal device 662, the de-cap device 664, the analyzer devices 666, the re-seal device 668, the storage and retrieval module 670, and the output module 672. The transport system 652 comprises multiple belts 653, moved by one or more motors 655, carrying transport containers 657 for carrying the blood sample tubes 16. In one embodiment, the transport system 652 may comprise the Accelerator APS, manufactured by Inpeco SA and distributed by Abbott Laboratories. In other embodiments, the transport system 652 may vary in quantities, type, and function.

The robot system 654 comprises one or more robots 659 which are for moving the blood sample tubes 16 at or between one or more of the transport system 652, the input module 656, the identification device 658, the centrifuge device 660, the de-seal device 662, the de-cap device 664, the analyzer devices 666, the re-seal device 668, the storage and retrieval module 670, and the output module 672. In one embodiment, the robot system 654 may comprise model TX40, manufactured by Staubli. In other embodiments, the robot system 654 may vary in quantities, type, and function.

The input module 656 is for supplying the blood sample tubes 16. In one embodiment, the input module 656 may comprise the Input Output Module, manufactured by Inpeco SA and distributed by Abbott Laboratories. In other embodiments, the input module 656 may vary in quantities, type, and function. The identification device 658 is for identifying one or more features of the blood sample tubes 16. For instance, the identification device 658 may identify an identification of each blood sample tube 16, a size of each blood sample tube 16, a shape of each blood sample tube 16, or another characteristic of each blood sample tube 16. The identification device 658 may identify a type, or lack thereof, of blood additives 28 disposed within inner cavities 20 of the blood sample tubes 16 using indicators 14 attached to or comprising portions of the blood sample tubes 16, or may identify one or more other identifying features regarding the blood sample tubes 16. The indicators 14 may comprise any type of indicators disclosed herein. The identification device 658 may comprise a visual detection device for visually detecting the indicators 14 of the blood sample tubes 16. In one embodiment, the identification device 658 may comprise model FM-4V manufactured by JADAK. In other embodiments, the identification device 658 may vary in quantities, type, and function.

The centrifuge device 660 is for applying a centrifugal force to the blood sample tubes 16. In one embodiment, the centrifuge device 660 may comprise model Rotanta 460 RSC, manufactured by Hettich. In other embodiments, the centrifuge device 660 may vary in quantities, type, and function. The de-seal 662 is for de-sealing seals of the blood sample tubes 16. In one embodiment, the de-seal device 662 may comprise the desealer module manufactured by Inpeco and distributed by Abbott Laboratories. In other embodiments, the de-seal device 662 may vary in quantities, type, and function. The de-cap device 664 is for removing the caps 12 of the blood sample tubes 16 leaving indicators 14 attached to or still comprising a portion of the blood sample tubes 16. The caps 12 comprise any type of the caps disclosed herein. In one embodiment, the de-cap device 664 may comprise the decapper module, manufactured by Inpeco and distributed by Abbott Laboratories. In other embodiments, the de-cap device 664 may vary in quantities, type, and function. The one or more analyzer devices 666 are for analyzing the blood samples 30 contained in the blood sample tubes 16. Each of the one or more analyzer devices 666 may conduct different types of analysis on the blood samples 30. In another embodiment, each of the one or more analyzer devices 666 may conduct the same types of analysis on the blood samples 30. In one embodiment, the analyzer devices 666 may comprise any of models ARCHITECT c8000 or c16000 manufactured by Toshiba and Abbott Laboratories or the ARCHITECT i2000sr manufactured by Abbott Laboratories. In other embodiments, the analyzer devices 666 may vary in quantity, model, type, and function.

The re-seal device 668 is for re-applying seals and/or cap 12 to the blood sample tubes 16. In one embodiment, the re-seal device 668 may comprise the resealer module manufactured by Inpeco and distributed by Abbott Laboratories. In other embodiments, the re-seal device 668 may vary in quantities, type, and function. The storage and retrieval module 670 is for storing and retrieving the blood sample tubes 16. In one embodiment, the storage and retrieval module 670 may comprise the storage module, manufactured by Inpeco and distributed by Abbott Laboratories. In other embodiments, the storage and retrieval module 670 may vary in quantities, type, and function. The output module 672 is for outputting the blood sample tubes 16. In one embodiment, the output module 672 may comprise the Input Output Module, manufactured by Inpeco and distributed by Abbott Laboratories. In other embodiments, the output module 672 may vary in quantities, type, and function. For instance, in one embodiment the output module 672 may be combined with input module 656. The output module 672 may output the sample tubes 16 to varying types of testing, analysis, transport, storage, or waste devices 674. In still other embodiments, the automatic blood sample handling system 650 may comprise components of a varying number, type, and function for processing and handling blood samples 30 contained in blood sample tubes 16.

Figure 16:
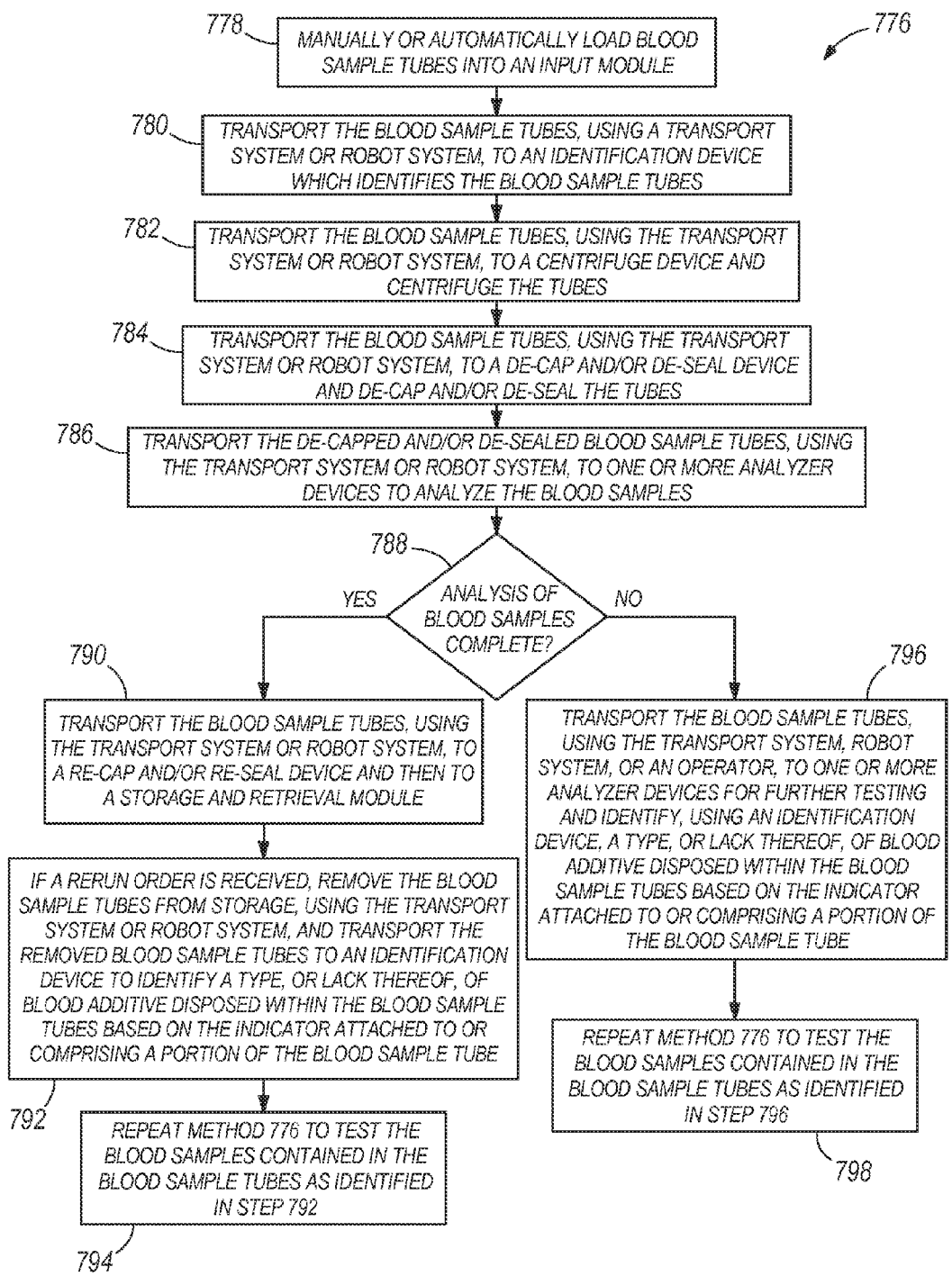
FIG. 16 illustrates one embodiment of a method for automatically identifying a type, or lack thereof, of blood additive disposed within a blood sample tube.

FIG. 16 illustrates one embodiment of a method 776 for automatically identifying a type, or lack thereof, of blood additive disposed within a blood sample tube. In step 778, blood sample tubes are loaded manually or automatically into an input module of an automatic blood sample handling system. In step 780, a transport system or robot system transports the blood sample tubes to an identification device which identifies the blood sample tubes. In step 782, the transport system or robot system transports the blood sample tubes to a centrifuge device which applies a centrifuge force to the blood sample tubes. In step 784, the transport system or robot system transports the blood sample tubes to a de-cap device which removes the caps from the blood sample tubes leaving indicators attached to or comprising portions of the blood sample tubes. During step 784, the transport system or robot system may further transport the blood sample tubes to a de-seal device which may remove one or more seals from the blood sample tubes. In step 786, the transport system or robot system transports the de-capped and/or de-sealed blood sample tubes to one or more analyzer devices which analyze the blood samples in the blood sample tubes. In step 788, a decision is made as to whether the analysis of the blood samples is complete.

If the analysis of the blood samples is determined to be complete during step 788, in step 790 the transport system or robot system transports the blood sample tubes to a re-seal device which recaps and/or reseals the blood sample tubes, and then transports the resealed and/or recapped blood sample tubes to a storage and retrieval module. In step 792, if a rerun order is received the transport system or robot system removes the blood sample tubes from storage and transports the removed blood sample tubes to an identification device which identifies a type, or lack thereof, of blood additive disposed within the blood sample tubes based on the indicator attached to or comprising a portion of the blood sample tube. In step 794, any of the steps of the method 776 may be repeated to test the blood samples contained in the blood sample tubes as identified in step 792.

On the other hand, if the analysis of the blood samples is determined to be incomplete during step 788, in step 796 the transport system, robot system, or an operator transports the blood sample tubes to one or more analyzer devices for further testing. During step 796, an identification device identifies a type, or lack thereof, of blood additive disposed within the blood sample tubes based on the indicator attached to or comprising a portion of the blood sample tube. In step 798, any of the steps of the method 776 may be repeated to test the blood samples contained in the blood sample tubes as identified in step 796. It is noted that the steps of the method 776 are accomplished using one or more processors/controllers which may be internal or external to the referenced components. In other embodiments, the steps of the method 776 may be modified in order, one or more of the steps may be omitted, or additional steps may be added.

Figure 17:
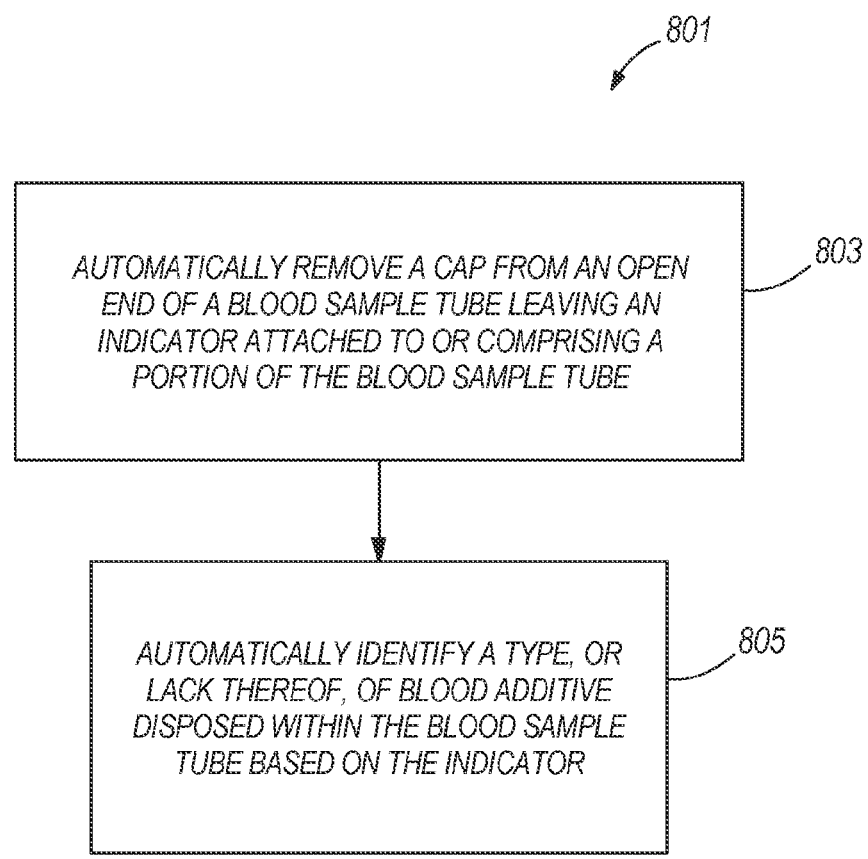
FIG. 17 illustrates one embodiment of a method for automatically identifying a type, or lack thereof, of blood additive disposed within a blood sample tube.

FIG. 17 illustrates one embodiment of a method 801 for automatically identifying a type, or lack thereof, of blood additive disposed within a blood sample tube. In step 803, a cap is automatically removed from an open end of a blood sample tube leaving an indicator attached to or comprising a portion of the blood sample tube. If the indicator comprises a label, it extends around at least half of a perimeter of the blood sample tube, at least 75 percent of the perimeter of the blood sample tube, or around an entire perimeter of the blood sample tube. The indicator may comprise any of the following embodiments: a color, shape, size, or other identifying feature; a ring; a color which may comprise a same color as the cap or a different color; a portion of the blood sample tube comprising a color, shape, size, or other identifying feature; an attachment to the blood sample tube; or another type of indicator. Step 803 may comprise any of the following embodiments: removing the cap with a de-cap device; detaching the cap from being directly attached to the indicator; removing the cap from being directly attached to the blood sample tube without the indicator being directly attached to the cap; removing the cap from the open end of the blood sample tube with the removed cap being attached to the indicator with a flexible member and the indicator being attached to the blood sample tube; detaching a female portion of the cap from a male portion of the indicator; or detaching a male portion of the cap from a female portion of the indicator. In step 805, a type, or lack thereof, of blood additive disposed within the blood sample tube is automatically identified based on the indicator. Step 805 may comprise an identification device, such as a visual detection device or other type of identification device, identifying visually or otherwise the type, or lack thereof, of the blood additive disposed within the blood sample tube based on the indicator. It is noted that the steps of the method 801 are accomplished using one or more processors/controllers which may be internal or external to the referenced components. In other embodiments, the steps of the method 801 may be modified in order, one or more of the steps may be omitted, or additional steps may be added.

Figure 18:
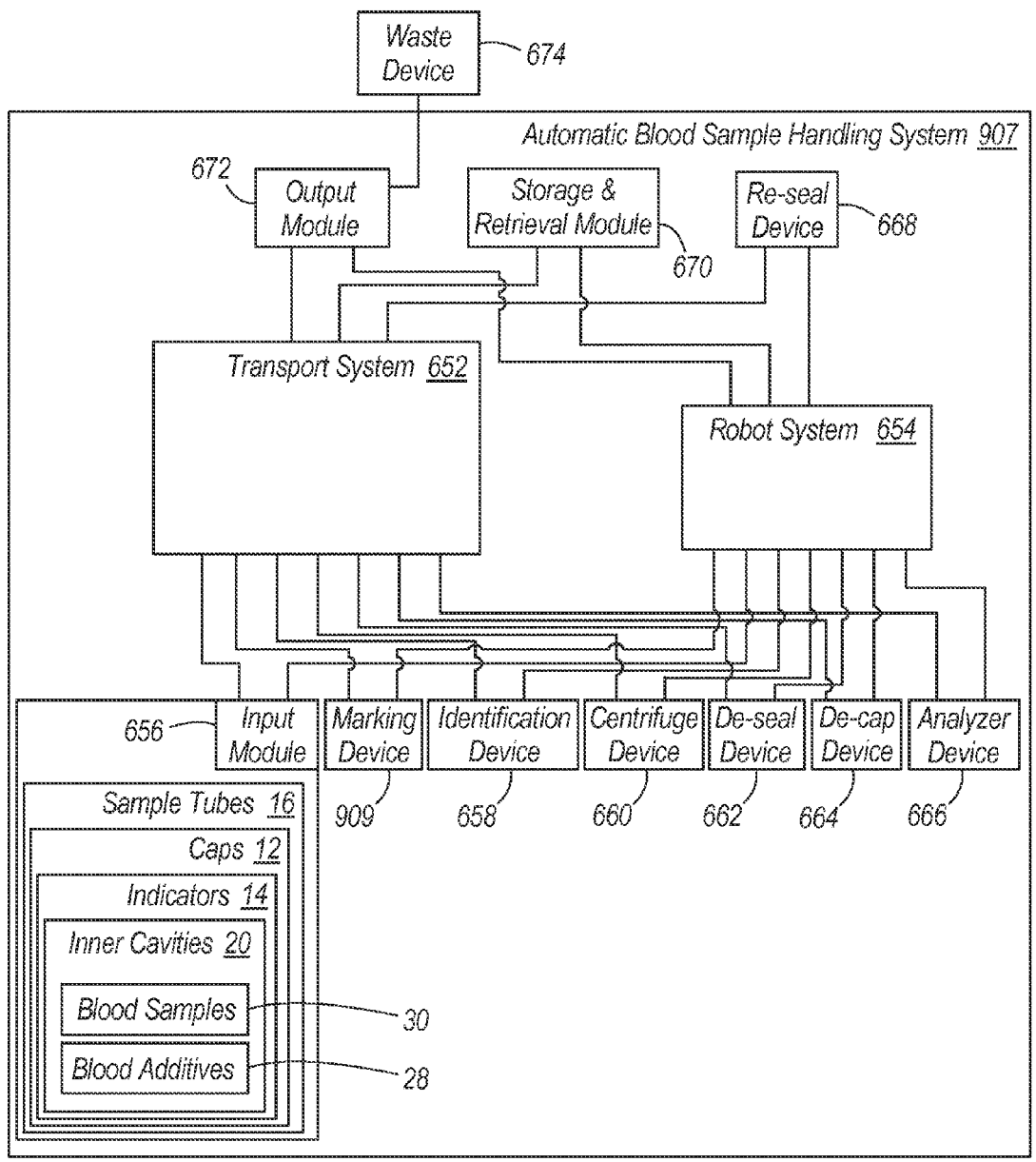
FIG. 18 illustrates a box diagram of another embodiment of an automatic blood sample handling system.

FIG. 18 illustrates a box diagram of another embodiment of an automatic blood sample handling system 907. Just as in the embodiment of FIG. 15, the blood sample handling system 907 comprises a transport system 652, a robot system 654, an input module 656, an identification device 658, a centrifuge device 660, a de-seal device 662, a de-cap device 664, analyzer devices 666, a re-seal device 668, a storage and retrieval module 670, and an output module 672. The only difference between the blood sample handling system 907 of FIG. 18 and the blood handling system 650 of FIG. 15 is that the blood sample handling system 907 of FIG. 18 further comprises a marking device 909. The marking device 909 is for automatically marking the blood sample tubes 16, carrying blood samples 30, with indicators 14 indicating a type, or lack thereof, of blood additives 28 disposed within the blood sample tubes 16. The marking device 909 may comprise a color-marking device, such as a painting device, an ink-jet device, a laser marking device, a printing device, or other type of color-marking device, for automatically marking the blood sample tubes 16 with color indicators 14 which may comprise a same color as the cap 12.

The identification device 658 may automatically identify a type, or lack thereof, of the blood additives 28 disposed within the blood sample tubes 16 based on the indicators 14 marked on the blood sample tubes 16 by the marking device 909. The identification device 658 may comprise a visual detection device for visually detecting the indicators 14 marked on the sample tubes 16, or another type of identification device. In one embodiment, the identification device 658 may be for automatically identifying a characteristic of the cap 12, such as a color, and the marking device 909 may be for automatically marking the blood sample tube 16 with the indicator 14 based on the characteristic of the cap 12 identified by the identification device 658. It is noted that any of the components of the blood handling system 907 may comprise their own processor/controller. In other embodiments, separate processor/controllers may be used to control the blood handling system 907.

Figure 19:
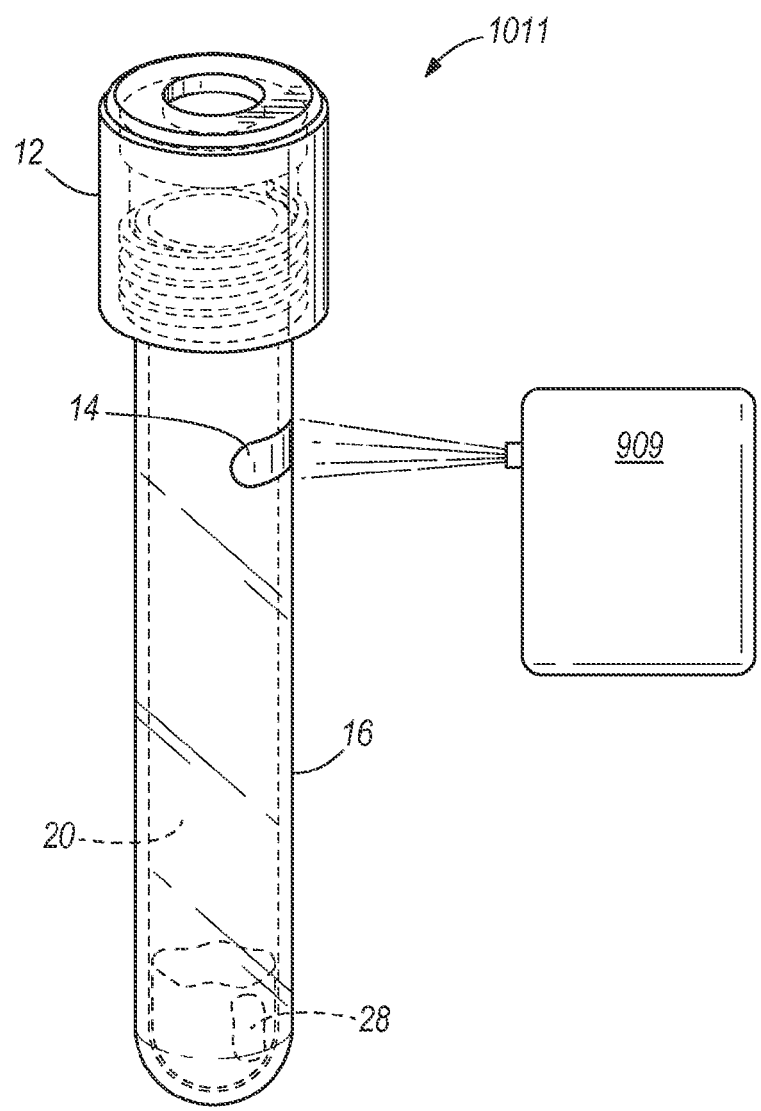
FIG. 19 illustrates a front perspective view of one embodiment of a blood sample apparatus with a cap attached to a blood sample tube with a marking device marking the blood sample tube with an indicator.

FIG. 19 illustrates a front perspective view of one embodiment of a blood sample apparatus 1011 with a cap 12 attached to a blood sample tube 16 with a marking device 909 marking the blood sample tube 16 with an indicator 14. The marking device 909 may mark the blood sample tube 16 with an indicator 14 comprising a printed color or another identifying marking, formed using varying devices, which identifies a type, or lack thereof, of the blood additive 28 disposed within an inner cavity 20 of the blood sample tube 16. In one embodiment, the marking device 909 may mark the blood sample tube 16 with an indicator 14 in a same color as the cap 12. In other embodiments, the marking device 909 may mark the blood sample tube 16 with varying markings which identify a type, or lack thereof, of the blood additive 28 disposed within the blood sample tube 16. It is noted that the marking device 909 may comprise its own processor/controller. In other embodiments, one or more separate processor/controllers may be used to control the marking device 909.

Figure 20:
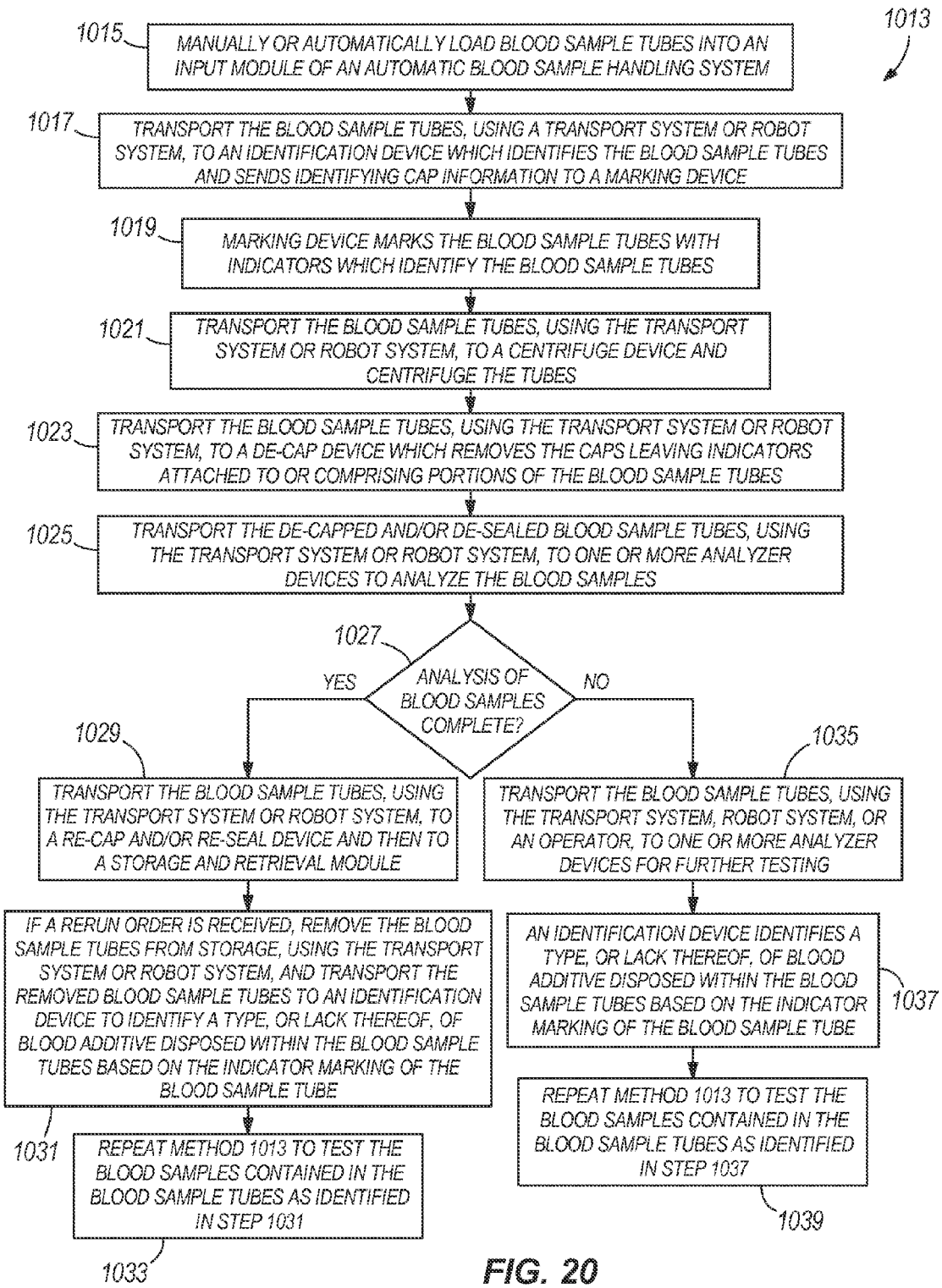
FIG. 20 illustrates one embodiment of a method for automatically identifying a type, or lack thereof, of blood additive disposed within a blood sample tube.

FIG. 20 illustrates one embodiment of a method 1013 for automatically identifying a type, or lack thereof, of blood additive disposed within a blood sample tube. In step 1015, blood sample tubes are loaded manually or automatically into an input module of an automatic blood sample handling system. In step 1017, a transport system or robot system transports the blood sample tubes to an identification device which identifies the blood sample tubes and which sends identifying cap information to a marking device. The identifying cap information may comprise a detected color of the cap or other detected information regarding the identified blood sample tubes. In step 1019, the marking device marks the blood sample tubes with indicators which identify the blood sample tubes. For instance, the marked indicators may identify a type, or lack thereof, of blood additives disposed within the blood sample tubes. The marking device may mark the blood sample tubes with indicators comprising a mark, a band, a strip, and/or a same color as the detected color of the cap. In step 1021, the transport system or robot system transports the blood sample tubes to a centrifuge device which applies a centrifuge force to the blood sample tubes. In step 1023, the transport system or robot system transports the blood sample tubes to a de-cap device which removes the caps from the blood sample tubes leaving indicators attached to or comprising portions of the blood sample tubes. During step 1023, the transport system or robot system may further transport the blood sample tubes to a de-seal device which may remove one or more seals from the blood sample tubes. In step 1025, the transport system or robot system transports the de-capped and/or de-sealed blood sample tubes to one or more analyzer devices which analyze the blood samples in the blood sample tubes. In step 1027, a decision is made as to whether the analysis of the blood samples is complete.

If the analysis of the blood samples is determined to be complete during step 1027, in step 1029 the transport system or robot system transports the blood sample tubes to a re-seal device which recaps and/or reseals the blood sample tubes, and then transports the resealed and/or recapped blood sample tubes to a storage and retrieval module. In step 1031, if a rerun order is received the transport system or robot system removes the blood sample tubes from storage and transports the removed blood sample tubes to an identification device which identifies a type, or lack thereof, of blood additive disposed within the blood sample tubes based on the indicator marking of the blood sample tube. In step 1033, any of the steps of the method 1013 may be repeated to test the blood samples contained in the blood sample tubes as identified in step 1031.

On the other hand, if the analysis of the blood samples is determined to be incomplete during step 1027, in step 1035 the transport system, robot system, or an operator transports the blood sample tubes to one or more analyzer devices for further testing. During step 1037, an identification device identifies a type, or lack thereof, of blood additive disposed within the blood sample tubes based on the indicator marking of the blood sample tube. In step 1039, any of the steps of the method 1013 may be repeated to test the blood samples contained in the blood sample tubes as identified in step 1037. It is noted that the steps of the method 1013 are accomplished using one or more processors/controllers which may be internal or external to the referenced components. In other embodiments, the steps of the method 1013 may be modified in order, one or more of the steps may be omitted, or additional steps may be added.

Figure 21:
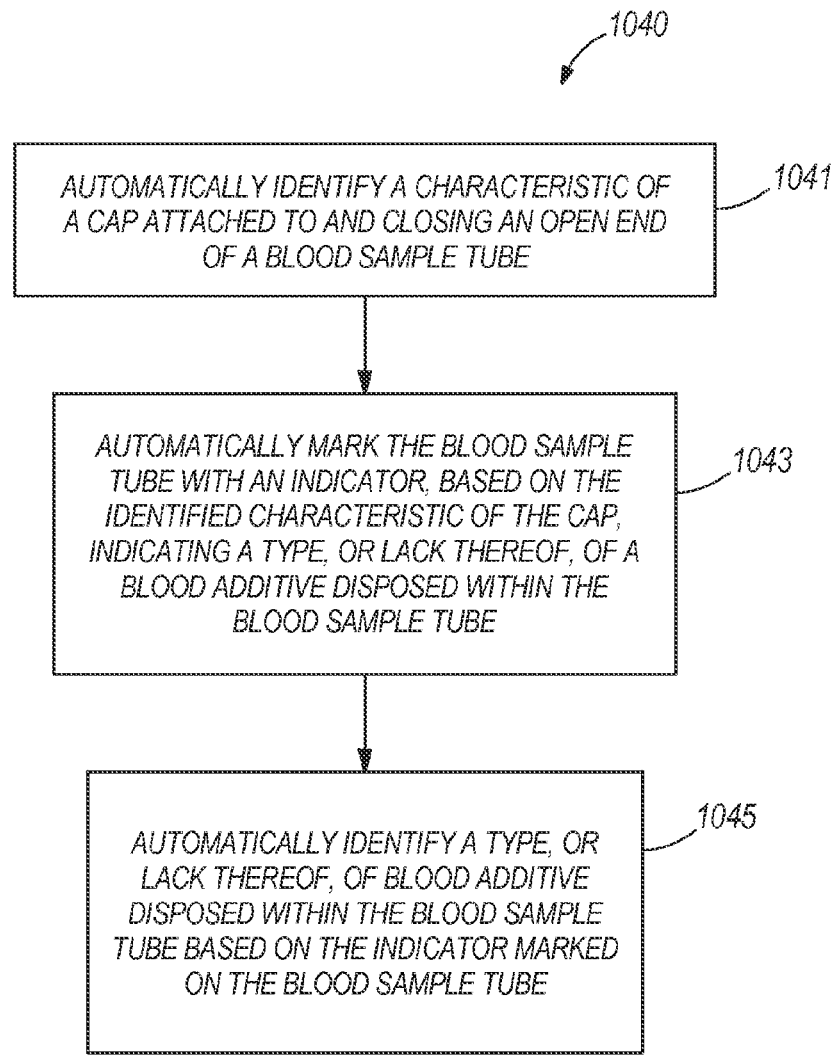
FIG. 21 illustrates one embodiment of a method for automatically identifying a type, or lack thereof, of blood additive disposed within a blood sample tube.

FIG. 21 illustrates one embodiment of a method 1040 for automatically identifying a type, or lack thereof, of blood additive disposed within a blood sample tube. In step 1041, a characteristic of a cap, attached to and closing an open end of a blood sample tube, is automatically identified. An identification device, such as a visual detection device or other type of identification device, may be used to automatically identify the characteristic of the cap attached to and closing the open end of the blood sample tube. The identified characteristic of the cap may comprise a color or another type of identifying characteristic. In step 1043, the blood sample tube is automatically marked with an indicator, based on the identified characteristic of the cap, indicating a type, or lack thereof, of a blood additive disposed within the blood sample tube. A marking device may be used to automatically mark the indicator on the blood sample tube. The indicator may comprise a color, a same color as the cap, or another type of indicator indicating the type, or lack thereof, of the blood additive disposed within the blood sample tube. In step 1045, the type, or lack thereof, of blood additive disposed within the blood sample tube may be automatically identified based on the indicator marked on the blood sample tube. An identification device, such as a visual detection device or other type of identification device, may be used to automatically identify the type, or lack thereof, of blood additive disposed within the blood sample tube based on the indicator marked on the blood sample tube. It is noted that the steps of the method 1040 are accomplished using one or more processors/controllers which may be internal or external to the referenced components. In other embodiments, the steps of the method 1040 may be modified in order, one or more of the steps may be omitted, or additional steps may be added.

One or more embodiments of the disclosure overcomes one or more issues of the existing art by providing apparatus and methods providing an indicator allowing for the automatic identification of the additive disposed within the blood sample tube after the cap is removed without the risk of the indicator being removed or covered up. This increases accuracy, reduces cost, and saves time during the testing of blood samples.

It should be understood, of course, that the foregoing relates to exemplary embodiments of the disclosure and that one or more modifications may be made without departing from the spirit and scope of the disclosure as set forth in the following claims.

We claim:

1. A blood sample apparatus comprising:
   a blood sample tube having an exterior surface, an inner cavity disposed within the exterior surface, and an open end;
   a cap closing the open end of the blood sample tube, the inner cavity under a vacuum-seal or connected to a suction device for drawing a blood sample into the inner cavity; and
   an indicator attached to or comprising a portion of the blood sample tube for indicating a type, or lack thereof, of blood additive disposed within the inner cavity, wherein when the cap is removed from the open end of the blood sample tube the indicator remains attached to or still comprises the portion of the blood sample tube, and if the indicator comprises a label it extends around at least half of a perimeter of the blood sample tube,
   wherein the blood sample tube comprises a female portion mated with a male portion of the indicator, or the blood sample tube comprises the male portion mated with the female portion of the indicator.

2. The blood sample apparatus of claim 1 wherein the indicator is directly detachable from the cap.

3. The blood sample apparatus of claim 1 wherein the indicator is directly attached to the blood sample tube and not directly attached to the cap.

4. The blood sample apparatus of claim 1 wherein the indicator is attached to the cap with a flexible member.

5. The blood sample apparatus of claim 1 wherein the indicator comprises a ring.

6. The blood sample apparatus of claim 1 wherein the indicator comprises a color.

7. The blood sample apparatus of claim 6 wherein the cap is the same color as the indicator.

8. The blood sample apparatus of claim 1 wherein the indicator comprises the portion of the blood sample tube, and the indicator comprises a color, shape, size, or identifying feature of the portion of the blood sample tube.

9. The blood sample apparatus of claim 2 wherein the indicator is attached to the cap with a breakable perforation which breaks when the cap is removed from the open end of the blood sample tube.

10. The blood sample apparatus of claim 1 wherein the indicator comprises the label extending around at least the half of the perimeter of the blood sample tube.

11. The blood sample apparatus of claim 10 wherein the label extends around at least 75 percent of the perimeter of the blood sample tube.

12. The blood sample apparatus of claim 10 wherein the label extends around the entire perimeter of the blood sample tube.

13. The blood sample apparatus of claim 1 wherein the blood sample tube comprises the female portion mated with the male portion of the indicator.

14. The blood sample apparatus of claim 1 wherein the blood sample tube comprises the male portion mated with the female portion of the indicator.

15. A blood sample apparatus comprising:
   a blood sample tube having an exterior surface, an inner cavity disposed within the exterior surface, and an open end;
   a cap closing the open end of the blood sample tube, the inner cavity under a vacuum-seal or connected to a suction device for drawing a blood sample into the inner cavity; and
   an indicator attached to or comprising a portion of the blood sample tube for indicating a type, or lack thereof, of blood additive disposed within the inner cavity, wherein when the cap is removed from the open end of the blood sample tube the indicator remains attached to or still comprises the portion of the blood sample tube, and if the indicator comprises a label it extends around at least half of a perimeter of the blood sample tube, wherein the blood sample tube is mechanically mated with the indicator.

16. The blood sample apparatus of claim 15 wherein the blood sample tube is mechanically mated with the indicator using a thread.

17. The blood sample apparatus of claim 15 wherein the blood sample tube is mechanically mated with the indicator using a snap-fit.

18. The blood sample apparatus of claim 15 wherein the blood sample tube is mechanically mated with the indicator using a friction fit.

19. The blood sample apparatus of claim 15 wherein the blood sample tube is mechanically mated with the indicator using male and female mating members.

* * * * *